(12) United States Patent
Hidalgo et al.

(10) Patent No.: US 6,238,404 B1
(45) Date of Patent: May 29, 2001

(54) MULTIPURPOSE MEDICAL DEVICE

(76) Inventors: Benito Hidalgo, 602 Portsmouth La., Foster City, CA (US) 94404; Alex Zapolanski, 555 Laurel Ave. #117, San Matco, CA (US) 94404

( * ) Notice: Subject to any disclaimer, the term of this patent is extended or adjusted under 35 U.S.C. 154(b) by 0 days.

(21) Appl. No.: 09/398,117

(22) Filed: Sep. 16, 1999

(51) Int. Cl.[7] .................................................. A61M 29/00
(52) U.S. Cl. ......................................... 606/148; 606/144
(58) Field of Search .................................. 606/191, 192, 606/145, 139, 144, 146–148, 223; 604/96

(56) References Cited

U.S. PATENT DOCUMENTS

| | | | |
|---|---|---|---|
| 4,623,327 | 11/1986 | Mahurkar | 128/668 |
| 4,643,194 | 2/1987 | Fogarty | 128/668 |
| 4,804,365 | * 2/1989 | Lizie et al. | 604/4 |
| 5,074,846 | 12/1991 | Clegg et al. | 604/164 |
| 5,352,198 | 10/1994 | Goldenberg et al. | 604/95 |
| 5,364,344 | 11/1994 | Beattie et al. | 604/43 |
| 5,364,374 | 11/1994 | Morrison et al. | 604/272 |
| 5,366,471 | 11/1994 | Jones et al. | 606/191 |
| 5,478,326 | * 12/1995 | Shiu | 604/264 |
| 5,807,326 | * 9/1998 | O'Neill et al. | 604/96 |
| 5,810,867 | 9/1998 | Zarbatany et al. | 606/191 |
| 5,830,196 | * 11/1998 | Hicks | 604/280 |
| 5,860,992 | * 1/1999 | Daniel et al. | 606/145 |

OTHER PUBLICATIONS

Fogarty Flexible Catheter (photographs).
Fogarty Bi–Pass Shunt (photograph).
DLP Coronary Artery Occluder (photograph) date: May 1991.

* cited by examiner

Primary Examiner—Michael H. Thaler
Assistant Examiner—Lien Ngo
(74) Attorney, Agent, or Firm—Mitchell Rosenfeld

(57) ABSTRACT

The present invention is a multipurpose medical device for use as a dilator, calibrator, suture guide and perfusion device. The device has an tapered, elongated tube; a valve having an opening coupled to the proximal end of the elongated tube; a connecting tube disengagably coupled to a second opening of the valve; a cylindrical sleeve slidably mounted on a portion of the elongated tubular member and having at least one radial groove configured for guiding a suture needle; and a plurality of diameter indicia marks located on the elongated tubular member. The cylindrical sleeve slides between a use position towards the distal end of the elongated tubular member and a park position towards the proximal end of the elongated tubular member.

17 Claims, 3 Drawing Sheets

MULTIPURPOSE MEDICAL DEVICE

FIELD OF THE INVENTION

The present invention relates to a multipurpose medical device, more particularly, a singular device configured for use as a vascular dilator, calibrator, occluder, suture guide and perfusion device.

BACKGROUND OF THE INVENTION

Numerous medical devices used for vascular dilation, calibration, suturing or perfusion are in existence. However, most devices are designed for providing a singular function. Designing a multipurpose medical device is a significant challenge in that the device must be cost effective to produce, reliable and the structures which provide each function must be complimentary rather than interfere with each other. Some existing devices do provide more than one function however none perform all of the functions that are accomplished by the present invention.

One example of a multipurpose device is the Fogarty® Flexible Calibrator manufactured by American Edwards Laboratories. This device is used as a dilator and calibrator, however it is not and can not be used for suturing or perfusion. Also, this device can only calibrate a single size, since the device has a uniform diameter. This is not cost effective since surgeons on average require 2.5 devices per patient per procedure to properly calibrate the size. At approximately $75 per device, which are single use only (i.e., disposed of after use in a patient), this is a significant cost. Another device which is sometimes used in place of the Fogarty® Flexible Calibrator is the metal olive tip probe. Although this device is reuseable, it is very traumatic to vessels as it is very hard and inflexible.

Other devices exist for performing singular functions. The Coronary Artery Occluder manufactured by DLP is a typical device that is used to occlude the coronary artery. This is done by inserting the device into the artery and suturing the device in place. Every 15 minutes the sutures and the device must be removed to allow for perfusion of fluids or blood to the artery. This is time consuming and must be performed by the surgeon.

The Fogarty® Bi-pass Shunt is used to bi-pass an artery from one end of a diseased segment to another in order to maintain blood flow. Catheter are known in the art for use as perfusion devices. On example of such a catheter is found in U.S. Pat. No. 5,364,344, which discloses a dual lumen catheter.

The lack of a multipurpose medical device that functions as a dilator, calibrator, occluder, suture guide and perfusion device is an important problem in the medical field. Currently, multiple devices must be used to perform these functions. This results in higher surgical costs since additional instruments must be used during surgery. Also, time is lost since a surgeon must switch from one instrument to another in order to perform these different functions, rather than smoothly transitioning from one function to the next with a single instrument. Additionally, time is lost every time the surgeon must remove an occluder and sutures to perfuse an artery and then re-insert the occluder and sutures. This means time that the surgeon must spend in the operating room and the patient is anesthetized. Switching from one instrument to another is also problematic in that the surgeons attention shifts from the hand off of the instrument from the nurse and away from the patient.

The present invention provides a multipurpose medical device that helps solves these problems by packaging a multitude of functions into a singular medical device. In particular, the present invention is intended to replace the Fogarty® Flexible Calibrator (or the metal olive tip probe), the DLP Coronary Artery Occluder, the Fogarty® Bi-pass Shunt and perfusion catheters with a singular device that provides these functions and more.

SUMMARY OF THE INVENTION

The present invention is a multipurpose medical device which functions as a vascular dilator, calibrator, suture guide and perfusion device. All of these functions are provided in a singular device An object of the invention is to combine multiple medical functions into a singular device.

Another object of the invention is to provide a multipurpose medical device where the structures which provide each function are complimentary and do not interfere with each other.

A further object of the invention is to provide a cost effective medical device where multiple functions are combined in a singular device.

It is also an object of the invention to provide a medical device which saves time normally lost when a surgeon must switch from one instrument to another in order to perform different functions.

Also, it is an object of the invention to provide a multipurpose medical device that allows smooth transitioning from one function to the next with a single instrument.

Additionally, it is also an object of the invention to provide a medical device which saves time normally lost every time the surgeon must remove an occluder and sutures to perfuse an artery and then re-insert the occluder and sutures.

Moreover, it is an object of the invention to provide a multipurpose medical device which reduces the time that the surgeon must spend in the operating room and the patient is anesthetized.

An additional object of the invention is to provide a multipurpose medical device which helps surgeons maintain attention on the patient rather than on the hand off of multiple instruments from the nurse.

Also, it is an object of the invention to provide a multipurpose medical device that reduces the risk of danger to vessels.

Another object of the invention is to provide a multipurpose medical device that is reliable and simple in construction.

The present invention is a multipurpose medical device for use as a dilator, calibrator, suture guide and perfusion device. The device has an tapered, elongated tube; a valve having an opening coupled to the proximal end of the elongated tube; a connecting tube disengagably coupled to a second opening of the valve; a cylindrical sleeve slidably mounted on a portion of the elongated tubular member and having at least one radial groove configured for guiding a suture needle; and a plurality of diameter indicia marks located on the elongated tubular member. The cylindrical sleeve slides between a use position towards the distal end of the elongated tubular member and a park position towards the proximal end of the elongated tubular member.

The present invention has other objects and advantages which are set forth in the description of the Best Mode of Carrying Out the Invention. The features and advantages described in the specification, however, are not all inclusive, and particularly, many additional features and advantages will be apparent to one of ordinary skill in the art in view of the drawings, specification, and claims herein.

DESCRIPTION OF THE PREFERRED EMBODIMENTS

Figure 1:
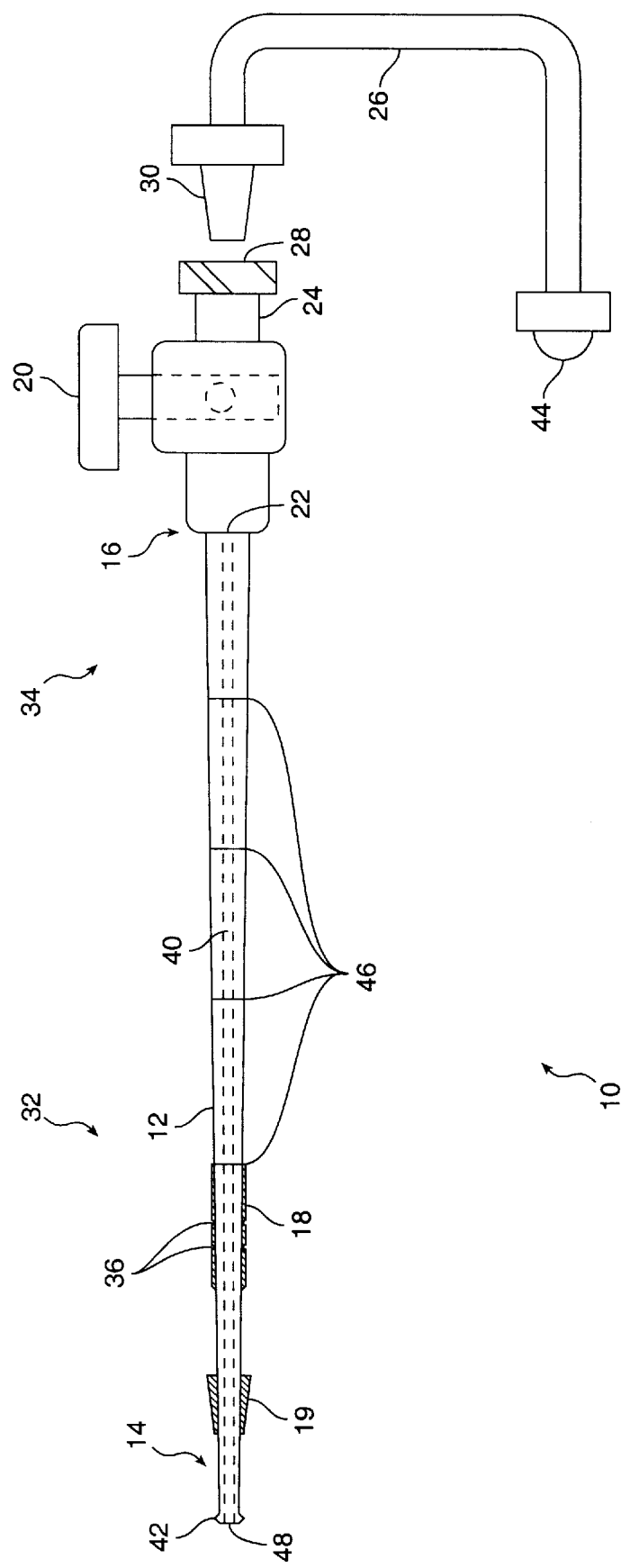
FIG. 1 is a side view of the multipurpose medical device of the present invention.

The present invention is a multipurpose medical device used as a combination dilator, calibrator, suture guide and perfusion device. As depicted in FIG. 1, multipurpose medical device 10 has an elongated tube 12 having a distal end 14 and proximal end 16, suture sleeve 18, stopper 19, valve 20 (which is preferably a 2-way or 3-way stop cock) having openings 22 and 24, and connecting tube 26. The use of a 3-way stop cock allows the device along with a transducer to provide an additional egress to elongated tube 12 for pressure monitoring. Elongated tube 12 is coupled to valve 20 by mounting distal end 16 of elongated tube 12 inside opening 22. When in use, elongated tube 12 is inserted into an artery or vein distal end 14 first. Opening 24 of valve 20 has a female coupling 28 for receiving male coupling 30 of connecting tube 26. Thus, connecting tube 26 is removably coupled to valve 20.

Figure 2:
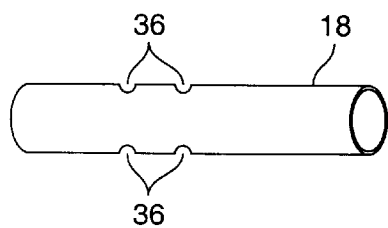
FIG. 2 is a side view of the suture sleeve shown in FIGS. 1 and 3.

Suture sleeve 18 (depicted in detail in FIG. 2), which is used to occlude coronary vessels while suturing anastomosis, is cylindrical in shape so that it can be slidably and removably mounted on elongated tube 12. Suture sleeve 18 may slide along elongated tube 12 between use position 32 proximate to distal end 14 and park position 34 proximate to proximal end 16. When at park position 34, suture sleeve 18 is stowed so that elongated tube can be used for dilation, calibration and perfusion without interference by suture sleeve 18. Sleeve 18 may slide along the entire length of elongated tube 12 (or if included as far as stopper 19 at distal end 14) and is held at any desired position by friction.

When in use position 32, suture sleeve 18 is used to aid in vascular suturing. At least one, but preferably two or more radial guide grooves 36 are formed in suture sleeve 18. Guide grooves 36 serve to guide a suture needle radially around suture sleeve 18 by riding the suture needle on one of guide grooves 36. Suture sleeve 18 is preferably made of an flexible atraumatic material such as silicone, pebax, polyolefins, polyethylene or polyurethane and sufficiently solid to resist a suture needle from piercing suture sleeve 18. Of these materials, pebax is optimal as it is stiffer to better prevent suture needle penetration. Alternately, a flexible metal such as stainless steel or nitinol could be used.

To facilitate the use of multipurpose device 10 for perfusion (i.e., directly injecting a fluid through a hole), elongated tube 12 is formed with an inner lumen 40 and blunt distal tip 42. Placing valve 20 in the open position allows fluids to pass through connecting tube 26, valve 20 and elongated tube 12 and out though distal opening 48. This is especially useful to perfuse distal arteries of the heart, because elongated tube 12 does not need to be removed from the artery while switching between occlusion and perfusion as required when switching between conventional devices like the the DLP Coronary Artery Occluder and a perfusion catheter.

This also allows for the testing of blood flow through inner lumen 40. A transducer is connected to valve 20 if a three-way stop cock is used or to connecting tube 26 if a two-way stop cock is used as valve 20 in order to test the blood pressure when valve 20 is opened. Alternately, a simple test for blood flow can be performed without a transducer by opening valve 20 to see if blood is forced out of connection tube 26.

Typically, a syringe is applied to aorta cell saver connection 44 on connecting tube 26. However, connecting tube 26 can be removed to allow a syringe to be coupled directly to valve 20 to inject fluids such as blood and plasma through elongated tube 12. Connecting tube 26 preferably is clear in order to see blood clots and air bubbles.

This function serves to replace the need for a bi-pass shunt which bi-passes a diseased vessel with blood flow from a native vessel (i.e., the segment proximal to the diseased segment). Multipurpose medical device 10 performs perfusion without the need for a shunt which like a shunt perfuses distal to the diseased segment with fresh blood supply. Rather than using the native vessel, multipurpose medical device 10 uses the blood from either aorta cell saver 44 which filters and oxygenates the patients own blood normally lost during surgery, directly from the aorta, from another artery, or from an external supply.

To facilitate the use of multipurpose medical device 10 as a dilator and as explained later a calibrator, elongated tube 12 is tapered from a larger diameter at proximal end 16 to a smaller diameter at distal end 14. Preferably, distal end 14 has a diameter between 1 and 3 mm with approximately 1.0 mm being optimal with blunt distal tip 42 being 1.5 mm, and proximal end 16 has a diameter between 3 and 8 mm with approximately 4.0 mm being optimal for coronary arteries. Other sizes may be preferable for other types of vessels.

The preferred length for elongated tube 12 is 25 cm, thus the diameter of elongated tube 12 tapers by 0.5 mm for every 5.0 cm in length. This results in a gradual uniform taper. For ease of construction, inner lumen 40 is not tapered. Additionally, elongated tube 12 is fabricated from a flexible atraumatic material such as silicone, pebax, polyolefins, polyethylene or polyurethane. These soft materials prevent damage to arteries that is common when using metal probes.

Figure 3B:
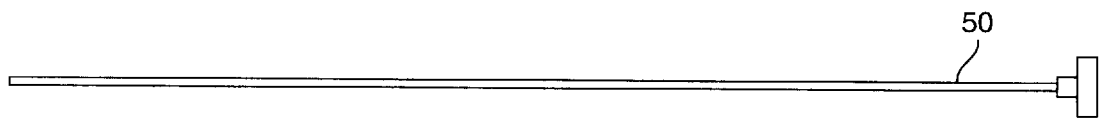
FIGS. 3A and 3B are side views of the multipurpose medical device of the present invention when used with a guide wire.
Figure 3A:
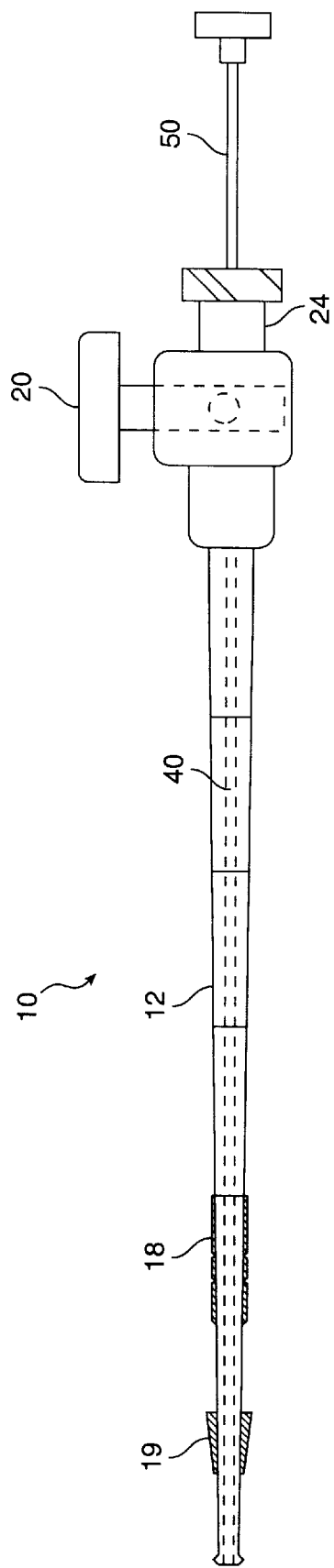

As depicted in FIGS. 3A and 3B, elongated tube 12 may be stiffened when necessary by inserting guide wire 50 into inner lumen 40. The diameter of inner lumen 40 (i.e., inner diameter of elongated tube 12) is preferably 0.031"–0.039" and optimally 0.035" +/– 0.002". This configuration is designed to accept a 0.030" guide wire. This configuration is useful to dilate coronary vessels before bypass as well as radial vessels because guide wire 50 allows elongated tube 12 in combination with guide wire 50 to be removably formable. In other words, elongated tube 12 and guide wire 50 can be bent to facilitate introduction into a vessel and then the bend and stiffness is eliminated from elongated tube 12 by removing guide wire 50 from inner lumen 40 via opening 24 in valve 20. Once guide wire 50 is removed, connecting tube 26 or any other device may be connected to valve 20. Guide wire 50 made of annealed ground stainless steel or nitinol so that it will hold its shape when bent. Once elongated tube 12 is introduced into a vessel, guide wire 50 should be removed and valve 20 should be closed when using multipurpose medical device 10 as a dilator.

Blunt distal tip 42 which is securely mounted on distal end 14 of elongated tube 12 also helps prevent damage to vessels by virtue of its smooth shape and material, and lack of sharp edges or points. Any sharp edges that may be found at the distal opening 48 of elongated tube 12 are covered by blunt distal tip 42 which can be formed from any of the same materials as elongated tube 12 but is formulated to be softer. Blunt distal tip 42 needs to be the softest of the materials which form multipurpose medical device 10 so that it is the least traumatic and less stiff than elongated tube 12. Blunt distal tip 42 also prevents suture sleeve 18 and stopper 19 from sliding off elongated tube 12 during use.

To facilitate the use of multipurpose medical device 10 as a calibrator, in addition to the taper of elongated tube 12, diameter indicia marks 46 are placed along elongated tube 12. Marks 46 indicate the diameter of elongated tube 12 at each marked location, which allows the diameter of a vessel to be determined by inserting elongated tube 12 into the vessel and noting the indicia mark 46 at the point at which the diameter of elongated 12 is the same as the vessel. This is useful for determining the size of a vein or artery to use as a graft and to know if the vessel is of sufficiently large diameter to even warrant a graft.

Preferably, a bio-compatible marker ink is used to place radial lines and numbers on elongated tube 12 as indicia marks 46. The preferred color is blue as it is readily discernible from the blood which will be on elongated tube 12 during use. Alternatively, multicolor inks may be used with each different color representing a different diameter range. The multicolor coding may also be done, although more costly, by changing the color of the material used to form elongated tube 12. Valve 20 should be closed when using multipurpose medical device 10 as a calibrator.

Figure 4A:
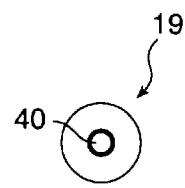
FIG. 4 is a front and side view of the stopper shown in FIGS. 1 and 3.
Figure 4B:
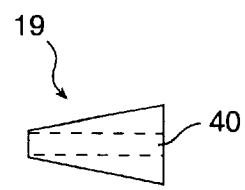

To facilitate the use of multipurpose medical device 10 as an occluder, stopper 19 (depicted in detail in FIG. 4) is slidably mounted on elongated tube 12. If suture sleeve 18 is included with device 10, stopper 19 is positioned between blunt distal tip 42 and suture sleeve 18. Stopper 19 is sufficiently wide in order to block (i.e. occlude) the vessel into which it is inserted. To facilitate the occlusion, stopper 19 is shaped as a truncated cone (i.e., a tapered cyclinder) which has its widest diameter toward proximal end 16. Preferably, stopper 19 has an inner diameter of 1.0 mm, an outer diameter which tapers from 4.0 mm at the proximal end to 1.0 mm at the distal end, and is 10–30 mm in length with 30 mm being optimal. Also, stopper 19 is made form the same materials as blunt distal tip 42, elongated tube 12 and suture sleeve 18 but is formulated to have a softness similar to blunt distal tip 42 to minimize trauma, sufficient elasticity so that is can slide the entire length of elongated tube 12, and sufficient flexibility to allow it to easily compress to fit into a vessel opening without causing trauma. Stopper 19 is held in any desired location on elongated tube 12 by friction. Thus, stopper 19 is atraumatic, flexible and slidable.

Unlike with conventional occluders, multipurpose medical device 10 and stopper 19 do not need to be removed from the vessel being occluded in order to allow perfusion of the vessel. Very simply, valve 20 is opened and fluids are introduced via connection tube 26. This procedure is sufficiently simple that the responsibility for performing the perfusion can be handed over from the surgeon to a nurse or perfusionist, thus saving the surgeon's valuable time.

Multipurpose medical device 10 may be packaged and shipped without suture sleeve 18 and stopper 19. This reduces the cost when these features are not needed for a given surgical procedure.

From the above description, it will be apparent that the invention disclosed herein provides a novel and advantageous multipurpose medical device. The foregoing discussion discloses and describes merely exemplary methods and embodiments of the present invention. One skilled in the art will readily recognize from such discussion that various changes, modifications and variations may be made therein without departing from the spirit and scope of the invention. Accordingly, disclosure of the present invention is intended to be illustrative, but not limiting, of the scope of the invention, which is set forth in the following claims.

We claim:

1. A multipurpose medical device comprising:
    an intravascular elongated tubular member having a proximal end and a distal end wherein the elongated tubular member tapers from a large diameter at the proximal end to a narrower diameter at the distal end;
    a valve having at least a first and second opening, the first opening being coupled to the proximal end of the elongated tubular member;
    a connecting tube disengagably coupled to the second opening of the valve;
    an intravascular cylindrical sleeve slidably mounted on a portion of the elongated tubular member and having at least on radial groove configured for guiding a suture needle; and
    a plurality of diameter indicia marks located on the elongated tubular member,
    wherein the intravascular cylindrical sleeve slides between a use position towards the distal end of the elongated tubular member and a park position towards the proximal end of the elongated tubular member.

2. The multipurpose medical device recited in claim 1 further comprising:
    a blunt tip at the distal end of the elongated tubular member.

3. The multipurpose medical device recited in claim 1 wherein the indicia marks are formed by bio-compatible marker ink.

4. The multipurpose medical device recited in claim 1 wherein the indicia marks are formed by radial lines and numbers.

5. The multipurpose medical device recited in claim 1 wherein the valve is a stop cock.

6. The multipurpose medical device recited in claim 1 wherein the elongated tubular member tapers from approximately 4.0 mm at the proximal end to approximately 1.5 mm at the distal end.

7. The multipurpose medical device recited in claim 1 further comprising:
    an aorta cell saver connection at the end of the connecting tube not coupled to the valve.

8. The multipurpose medical device recited in claim 1 further comprising:
    an inner lumen formed in the elongated tubular member for accommodating a guide wire.

9. The multipurpose medical device recited in claim 1 further comprising:
    a stopper slidably mounted on the elongated tubular member where in the stopper occludes a vessel when introduced therein.

10. A multipurpose medical device comprising:
    an intravascular elongated tubular member having a proximal end and a distal end wherein the elongated tubular member tapers from a larger diameter at the proximal end to a narrower diameter at the distal end;
    an inner lumen formed in the elongated tubular member;

an opening at the distal end of the elongated tubular member;

a formable guide wire removably located in the inner lumen, and an intravascular cylindrical sleeve slidably mounted on a portion of the elongated tubular member and having at least on radial groove configured for guiding a suture needle.

11. The multipurpose medical device recited in claim 10 further comprising:

a valve having at least a first and second opening, the first opening being coupled to the proximal end of the elongated tubular member.

12. The multipurpose medical device recited in claim 10 further comprising:

a plurality of diameter indicia marks located on the elongated tubular member.

13. The multipurpose medical device recited in claim 10 wherein the cylindrical sleeve slides between a use position towards the distal end of the elongated tubular member and a park position towards the proximal end of the elongated tubular member.

14. The multipurpose medical device recited in claim 10 further comprising:

a stopper slidably mounted on the elongated tubular member where in the stopper occludes a vessel when introduced therein.

15. A multipurpose medical device comprising:

an intravascular elongated tubular member having a proximal end and a distal end;

an inner lumen formed in the elongated tubular member;

an opening at the distal end of the elongated tubular member;

a formable guide wire removably located in the inner lumen;

an intravascular cylindrical sleeve slidably mounted on a portion of the elongated tubular member and configured for guiding a suture needle; and wherein the stopper occludes a vessel when introduced therein.

16. The multipurpose medical device recited in claim 15 further comprising:

at least one radial groove on the cylindrical sleeve for guiding a suture needle.

17. The multipurpose medical device recited in claim 15 wherein the elongated tubular member tapers from a larger diameter at the proximal end to a narrower diameter at the distal end.

* * * * *